US007744611B2

(12) United States Patent
Nguyen et al.

(10) Patent No.: US 7,744,611 B2
(45) Date of Patent: Jun. 29, 2010

(54) MINIMALLY INVASIVE VALVE REPAIR PROCEDURE AND APPARATUS

(75) Inventors: John D. Nguyen, San Jose, CA (US); Laurent Schaller, Los Altos, CA (US); Arthur Hill, Sausalito, CA (US)

(73) Assignee: Medtronic, Inc., Minneapolis, MN (US)

( * ) Notice: Subject to any disclaimer, the term of this patent is extended or adjusted under 35 U.S.C. 154(b) by 971 days.

(21) Appl. No.: 10/718,236

(22) Filed: Nov. 19, 2003

(65) Prior Publication Data
US 2004/0111099 A1 Jun. 10, 2004

Related U.S. Application Data

(63) Continuation of application No. 09/686,004, filed on Oct. 10, 2000, now Pat. No. 6,926,730.

(51) Int. Cl.
*A61B 17/08* (2006.01)
*A61B 17/04* (2006.01)
(52) U.S. Cl. ...................... 606/151; 606/232
(58) Field of Classification Search ............... 604/ 101.01-102.03; 606/72, 75, 219, 220, 232, 606/233, 142, 224, 153; 623/1.47
See application file for complete search history.

(56) References Cited

U.S. PATENT DOCUMENTS 43,098 A 6/1864 Cooper
(Continued)

FOREIGN PATENT DOCUMENTS

DE 0219999 3/1910
(Continued)

OTHER PUBLICATIONS

Maisano, F. et al. The Double Orifice Technique as a Standardized Approach to Treat Mitral Regurgitation Due to Severe Myxomatous Disease: Surgical Technique (European Journal of Cardiothoracic Surgery, vol. 17 (2000) 201 -205).
Chitwood Jr., W. Randolph. Mitral Valve Repair: Ischemic (Mastery of Cardiothoracic Surgery, Lippencott-Raven Publishers (1998) 309-321).
Written Opinion PCT/US01/31709 of Nov. 12, 2002.
International Search Report PCT/US01/31709 of Jan. 17, 2002.
"VCS Clip Applier System," published in 1995 by Auto Suture Company, a Division of U.S. Surgical Corporation.
(Continued)

*Primary Examiner*—Julian W Woo
(74) *Attorney, Agent, or Firm*—MIke Jaro; Jeffrey J. Hohenshell

(57) ABSTRACT

A clip of a self-closing type is used for valve repair. The clip is generally U-shaped with two end points separated from each other when it is constrained to be in an open configuration, but tends to coil up to assume its natural closed configuration if the constraint is removed. At least one end point is connected through a suture to a tissue-penetrating needle. A needle holder has an outer tube and an inner member which has a slit at the front and is slidable inside the outer tube. They are designed such that the slit can grab the needle tightly or release it as the inner member is moved backward or forward with respect to the outer tube. With the needle secured at the front, the needle holder is passed through a cannula inserted through an incision and the needle penetrates the leaflets such that the clip can be positioned with its end points hooked to the pair of leaflets to be stitched together. If the clip is released from the suture thereafter, it tends to coil up, reducing the distance between the end points and pulling the leaflets together. A double-arm clip assembly with each of the end points of the clip attached through a suture to a separate needle may be similarly used for valve repair. Such a double-arm clip assembly may contain two of such clips mutually connected by means of a flexible connector such that two leaflets are held together by the connector, with the two clips each anchored to a corresponding one of the leaflets.

17 Claims, 6 Drawing Sheets

U.S. PATENT DOCUMENTS

| | | |
|---|---|---|
| 636,728 A | 11/1899 | Kindel |
| 655,190 A | 8/1900 | Bramson |
| 1,087,186 A | 2/1914 | Scholfield |
| 1,167,014 A | 1/1916 | O'Brien |
| 1,539,221 A | 5/1925 | John |
| 1,583,271 A | 5/1926 | Biro |
| 1,625,602 A | 4/1927 | Gould et al. |
| 1,867,624 A | 7/1932 | Hoffman |
| 2,201,610 A | 5/1940 | Dawson |
| 2,240,330 A | 4/1941 | Flagg et al. |
| 2,256,382 A | 9/1941 | Dole |
| 2,264,679 A | 12/1941 | Ravel |
| 2,413,142 A | 12/1946 | Jones et al. |
| 2,430,293 A | 11/1947 | Howells |
| 2,505,358 A | 4/1950 | Gusberg et al. |
| 2,516,710 A | 7/1950 | Mascolo |
| 2,715,486 A | 8/1955 | Marcoff-Moghadam |
| 2,890,519 A | 6/1959 | Storz, Jr. |
| 2,940,452 A | 6/1960 | Smialowski |
| 3,055,689 A | 9/1962 | Jorgensen |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A | 9/1975 | Smith et al. |
| 3,908,662 A | 9/1975 | Razgulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A | 4/1989 | Leveen et al. |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A * | 3/1991 | Pyka et al. .................. 606/222 |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |

| | | | | | | |
|---|---|---|---|---|---|---|
| 5,119,983 A | | 6/1992 | Green et al. | 5,452,733 A | 9/1995 | Sterman et al. |
| 5,123,913 A | | 6/1992 | Wilk et al. | 5,454,834 A | 10/1995 | Boebel et al. |
| 5,127,413 A | | 7/1992 | Ebert | 5,456,246 A | 10/1995 | Schmiedling et al. |
| 5,129,913 A | | 7/1992 | Ruppert | 5,462,561 A | 10/1995 | Voda |
| 5,152,769 A | | 10/1992 | Baber | 5,474,557 A | 12/1995 | Mai |
| 5,154,189 A | | 10/1992 | Oberlander | 5,480,405 A | 1/1996 | Yoon |
| 5,158,566 A | | 10/1992 | Pianetti | 5,486,187 A | 1/1996 | Schenck |
| 5,171,250 A | | 12/1992 | Yoon | 5,486,197 A * | 1/1996 | Le et al. ................... 606/232 |
| 5,171,252 A * | | 12/1992 | Friedland .................. 606/151 | 5,488,958 A | 2/1996 | Topel et al. |
| 5,174,087 A | | 12/1992 | Bruno | 5,496,334 A | 3/1996 | Klundt et al. |
| 5,178,634 A | | 1/1993 | Ramos Martinez | 5,499,990 A | 3/1996 | Schulken et al. |
| 5,192,294 A | | 3/1993 | Blake | 5,500,000 A | 3/1996 | Feagin et al. |
| 5,196,022 A | | 3/1993 | Bilweis | 5,522,884 A | 6/1996 | Wright |
| 5,201,880 A | | 4/1993 | Wright et al. | 5,527,342 A * | 6/1996 | Pietrzak et al. ............. 606/232 |
| 5,207,694 A | | 5/1993 | Broome | 5,533,236 A | 7/1996 | Tseng |
| 5,217,027 A | | 6/1993 | Hermens | 5,538,509 A | 7/1996 | Dunlap et al. |
| 5,219,358 A | | 6/1993 | Bendel et al. | 5,545,214 A | 8/1996 | Stevens |
| 5,221,259 A | | 6/1993 | Weldon et al. | 5,549,619 A | 8/1996 | Peters et al. |
| 5,222,961 A | | 6/1993 | Nakao et al. | 5,556,411 A | 9/1996 | Taoda et al. |
| 5,222,976 A | | 6/1993 | Yoon | 5,562,685 A | 10/1996 | Mollenauer et al. |
| 5,234,447 A | | 8/1993 | Kaster et al. | 5,569,205 A | 10/1996 | Hart et al. |
| 5,236,440 A | | 8/1993 | Hlavacek | 5,569,274 A | 10/1996 | Rapacki et al. |
| 5,242,456 A | | 9/1993 | Nash et al. | 5,569,301 A | 10/1996 | Granger et al. |
| 5,242,457 A | | 9/1993 | Akopov et al. | 5,571,119 A | 11/1996 | Atala |
| 5,246,443 A | | 9/1993 | Mai | 5,571,175 A | 11/1996 | Vanney et al. |
| 5,250,053 A | | 10/1993 | Snyder | 5,582,616 A | 12/1996 | Bolduc et al. |
| 5,258,011 A | | 11/1993 | Drews | 5,582,619 A | 12/1996 | Ken |
| 5,261,917 A | | 11/1993 | Hasson et al. | 5,584,879 A | 12/1996 | Reimold et al. |
| 5,269,783 A | | 12/1993 | Sander | 5,586,983 A | 12/1996 | Sanders et al. |
| 5,269,809 A | | 12/1993 | Hayhurst et al. | 5,591,179 A | 1/1997 | Edelstein |
| 5,282,825 A | | 2/1994 | Muck et al. | 5,593,414 A | 1/1997 | Shipp et al. |
| 5,290,289 A | | 3/1994 | Sanders et al. | 5,593,424 A | 1/1997 | Northrup, III |
| 5,304,117 A | | 4/1994 | Wilk | 5,597,378 A | 1/1997 | Jervis |
| 5,304,204 A | | 4/1994 | Bregen | 5,601,571 A | 2/1997 | Moss |
| 5,306,296 A | | 4/1994 | Wright et al. | 5,601,572 A | 2/1997 | Middleman et al. |
| 5,312,436 A | | 5/1994 | Coffey et al. | 5,601,600 A | 2/1997 | Ton |
| 5,314,468 A | | 5/1994 | Ramos Martinez | 5,603,718 A | 2/1997 | Xu |
| 5,330,503 A | | 7/1994 | Yoon | 5,609,608 A | 3/1997 | Bennett et al. |
| 5,334,196 A | | 8/1994 | Scott et al. | 5,628,757 A | 5/1997 | Hasson |
| 5,336,233 A | | 8/1994 | Chen | 5,630,540 A | 5/1997 | Blewett |
| 5,336,239 A | | 8/1994 | Gimpelson | 5,632,752 A | 5/1997 | Buelna |
| 5,346,459 A | | 9/1994 | Allen | 5,632,753 A | 5/1997 | Loeser |
| 5,350,420 A | | 9/1994 | Cosgrove et al. | 5,643,295 A | 7/1997 | Yoon |
| 5,353,804 A | | 10/1994 | Kornberg et al. | 5,643,305 A | 7/1997 | Al-Tameem |
| 5,355,897 A | | 10/1994 | Pietrafitta et al. | 5,645,568 A | 7/1997 | Chervitz et al. |
| 5,356,424 A | | 10/1994 | Buzerak et al. | 5,653,716 A | 8/1997 | Malo et al. |
| 5,364,406 A | | 11/1994 | Sewell | 5,653,718 A | 8/1997 | Yoon |
| 5,366,459 A | | 11/1994 | Yoon | 5,658,312 A | 8/1997 | Green et al. |
| 5,366,462 A | | 11/1994 | Kaster et al. | 5,660,186 A | 8/1997 | Bachir |
| 5,366,479 A | | 11/1994 | McGarry et al. | 5,665,109 A | 9/1997 | Yoon |
| 5,374,268 A * | | 12/1994 | Sander ...................... 606/72 | 5,669,918 A | 9/1997 | Balazs et al. |
| 5,376,096 A | | 12/1994 | Foster | 5,676,670 A | 10/1997 | Kim |
| 5,382,259 A | | 1/1995 | Phelps et al. | 5,683,417 A | 11/1997 | Cooper |
| 5,383,904 A | | 1/1995 | Totakura et al. | 5,690,662 A | 11/1997 | Chiu et al. |
| 5,387,227 A | | 2/1995 | Grice | 5,695,504 A | 12/1997 | Gifford, III et al. |
| 5,403,331 A | | 4/1995 | Chesterfield | 5,695,505 A | 12/1997 | Yoon |
| 5,403,333 A | | 4/1995 | Kaster et al. | 5,697,913 A | 12/1997 | Sierocuk et al. |
| 5,403,338 A | | 4/1995 | Milo | 5,697,943 A | 12/1997 | Sauer et al. |
| 5,403,346 A | | 4/1995 | Loeser | 5,700,270 A | 12/1997 | Peyser et al. |
| 5,413,584 A | | 5/1995 | Schulze | 5,700,271 A | 12/1997 | Whitfield et al. |
| 5,413,597 A * | | 5/1995 | Krajicek .................. 623/1.47 | 5,702,412 A | 12/1997 | Popov et al. |
| 5,417,684 A | | 5/1995 | Jackson et al. | 5,707,362 A | 1/1998 | Yoon |
| 5,417,700 A | | 5/1995 | Egan | 5,707,380 A | 1/1998 | Hinchliffe et al. |
| 5,423,821 A | | 6/1995 | Pasque | 5,709,693 A | 1/1998 | Taylor |
| 5,431,666 A | | 7/1995 | Sauer et al. | 5,709,695 A | 1/1998 | Northrup, III |
| 5,437,680 A | | 8/1995 | Yoon | 5,715,987 A | 2/1998 | Kelley et al. |
| 5,437,681 A | | 8/1995 | Meade et al. | 5,720,755 A | 2/1998 | Dakov |
| 5,437,685 A | | 8/1995 | Blasnik | 5,725,539 A | 3/1998 | Matern |
| 5,439,479 A * | | 8/1995 | Shichman et al. .......... 606/220 | 5,725,542 A | 3/1998 | Yoon |
| 5,445,167 A | | 8/1995 | Yoon et al. | 5,728,135 A | 3/1998 | Bregen et al. |
| 5,445,644 A | | 8/1995 | Pietrafitta et al. | 5,732,872 A | 3/1998 | Bolduc et al. |
| 5,450,860 A | | 9/1995 | O'Connor | 5,735,290 A | 4/1998 | Sterman et al. |
| 5,451,231 A | | 9/1995 | Rabenau et al. | 5,746,753 A | 5/1998 | Sullivan et al. |

| | | | | | |
|---|---|---|---|---|---|
| 5,755,778 A | 5/1998 | Kleshinski | 5,997,556 A | 12/1999 | Tanner |
| 5,766,189 A | 6/1998 | Matsumo | 6,001,110 A | 12/1999 | Adams |
| 5,769,870 A | 6/1998 | Salahich et al. | 6,007,544 A | 12/1999 | Kim |
| 5,779,718 A | 7/1998 | Green et al. | 6,010,531 A | 1/2000 | Donlon et al. |
| 5,782,397 A | 7/1998 | Koukline | 6,013,084 A | 1/2000 | Ken et al. |
| 5,782,844 A | 7/1998 | Yoon et al. | 6,022,367 A | 2/2000 | Sherts |
| 5,797,920 A | 8/1998 | Kim | 6,024,748 A | 2/2000 | Manzo et al. |
| 5,797,933 A | 8/1998 | Snow et al. | 6,032,849 A | 3/2000 | Mastri et al. |
| 5,797,934 A | 8/1998 | Rygaard | 6,033,419 A | 3/2000 | Hamblin, Jr. et al. |
| 5,797,960 A | 8/1998 | Stevens et al. | 6,036,699 A | 3/2000 | Andreas et al. |
| 5,799,661 A | 9/1998 | Boyd et al. | 6,036,703 A | 3/2000 | Evans et al. |
| 5,799,857 A | 9/1998 | Robertson et al. | 6,036,710 A | 3/2000 | McGarry et al. |
| 5,810,848 A | 9/1998 | Hayhurst | 6,042,607 A | 3/2000 | Williamson et al. |
| 5,810,851 A | 9/1998 | Yoon | 6,056,751 A | 5/2000 | Fenton |
| 5,810,853 A | 9/1998 | Yoon | 6,063,070 A | 5/2000 | Eder |
| 5,810,882 A | 9/1998 | Bolduc et al. | 6,066,148 A | 5/2000 | Rygaard |
| 5,817,113 A | 10/1998 | Gifford, III et al. | 6,074,401 A | 6/2000 | Gardiner et al. |
| 5,820,631 A | 10/1998 | Nobles | 6,074,418 A | 6/2000 | Buchanan et al. |
| 5,824,002 A | 10/1998 | Gentelia et al. | 6,077,291 A | 6/2000 | Das |
| 5,824,008 A | 10/1998 | Bolduc et al. | 6,080,114 A | 6/2000 | Russin |
| 5,827,265 A | 10/1998 | Glinsky et al. | 6,083,237 A | 7/2000 | Huitema et al. |
| 5,827,316 A | 10/1998 | Young et al. | 6,106,538 A | 8/2000 | Shiber |
| 5,830,221 A | 11/1998 | Stein et al. | 6,110,188 A | 8/2000 | Narciso |
| 5,830,222 A | 11/1998 | Makower | 6,113,611 A | 9/2000 | Allen et al. |
| 5,833,698 A | 11/1998 | Hinchliffe | 6,113,612 A | 9/2000 | Swanson et al. |
| 5,849,019 A | 12/1998 | Yoon | 6,120,524 A | 9/2000 | Taheri |
| 5,851,216 A | 12/1998 | Allen | 6,132,438 A | 10/2000 | Fleischman et al. |
| 5,855,614 A | 1/1999 | Stevens et al. | 6,139,540 A | 10/2000 | Rost et al. |
| 5,868,702 A | 2/1999 | Stevens et al. | 6,143,004 A | 11/2000 | Davis et al. |
| 5,868,763 A | 2/1999 | Spence et al. | 6,149,658 A | 11/2000 | Gardiner et al. |
| 5,871,528 A | 2/1999 | Camps et al. | 6,152,935 A | 11/2000 | Kammerer et al. |
| 5,879,371 A | 3/1999 | Gardiner et al. | 6,152,937 A | 11/2000 | Peterson et al. |
| 5,881,943 A | 3/1999 | Heck et al. | 6,159,165 A | 12/2000 | Ferrera et al. |
| 5,882,340 A | 3/1999 | Yoon | 6,159,225 A | 12/2000 | Makower |
| 5,891,130 A | 4/1999 | Palermo et al. | 6,165,183 A | 12/2000 | Kuehn et al. |
| 5,891,160 A | 4/1999 | Williamson, IV et al. | 6,165,185 A | 12/2000 | Shennib et al. |
| 5,893,369 A | 4/1999 | LeMole | 6,171,320 B1 | 1/2001 | Monassevitch |
| 5,893,865 A | 4/1999 | Swindle et al. | 6,171,321 B1 | 1/2001 | Gifford, III et al. |
| 5,893,886 A | 4/1999 | Zegdi et al. | 6,176,413 B1 | 1/2001 | Heck et al. |
| 5,895,394 A | 4/1999 | Kienzle et al. | 6,176,864 B1 | 1/2001 | Chapman |
| 5,904,697 A | 5/1999 | Gifford, III et al. | 6,179,840 B1 | 1/2001 | Bowman |
| 5,908,428 A | 6/1999 | Scirica et al. | 6,179,848 B1 | 1/2001 | Solem |
| 5,911,352 A | 6/1999 | Racenet et al. | 6,179,849 B1 | 1/2001 | Yencho et al. |
| 5,919,207 A | 7/1999 | Taheri | 6,183,512 B1 | 2/2001 | Howanec et al. |
| 5,931,842 A | 8/1999 | Goldsteen et al. | 6,190,373 B1 | 2/2001 | Palermo et al. |
| 5,941,434 A | 8/1999 | Green | 6,193,733 B1 | 2/2001 | Adams |
| 5,941,442 A | 8/1999 | Geiste et al. | 6,193,734 B1 | 2/2001 | Bolduc et al. |
| 5,941,888 A | 8/1999 | Wallace et al. | 6,197,037 B1 | 3/2001 | Hair |
| 5,941,908 A | 8/1999 | Goldsteen et al. | 6,217,611 B1 | 4/2001 | Klostermeyer |
| 5,944,730 A | 8/1999 | Nobles et al. | 6,221,083 B1 | 4/2001 | Mayer |
| 5,951,576 A | 9/1999 | Wakabayashi | 6,241,738 B1 | 6/2001 | Dereume |
| 5,951,600 A | 9/1999 | Lemelson | 6,241,741 B1 | 6/2001 | Duhaylongsod et al. |
| 5,954,735 A | 9/1999 | Rygaard | 6,248,117 B1 | 6/2001 | Blatter |
| 5,957,363 A | 9/1999 | Heck | 6,250,308 B1 | 6/2001 | Cox |
| 5,957,938 A | 9/1999 | Zhu et al. | 6,254,615 B1 | 7/2001 | Bolduc et al. |
| 5,957,940 A | 9/1999 | Tanner et al. | 6,269,819 B1 | 8/2001 | Oz et al. |
| 5,961,481 A | 10/1999 | Sterman et al. | 6,280,460 B1 | 8/2001 | Bolduc et al. |
| 5,961,539 A | 10/1999 | Northrup, III et al. | 6,283,979 B1 | 9/2001 | Mers Kelly et al. |
| 5,964,772 A | 10/1999 | Bolduc et al. | 6,283,993 B1 | 9/2001 | Cosgrove et al. |
| 5,964,782 A | 10/1999 | Lafontaine et al. | 6,296,622 B1 | 10/2001 | Kurz et al. |
| 5,972,024 A | 10/1999 | Northrup, III et al. | 6,296,656 B1 | 10/2001 | Bolduc et al. |
| 5,976,159 A | 11/1999 | Bolduc et al. | 6,306,141 B1 | 10/2001 | Jervis |
| 5,976,161 A | 11/1999 | Kirsch et al. | 6,332,893 B1 | 12/2001 | Mortier et al. |
| 5,976,164 A | 11/1999 | Bencini et al. | 6,346,074 B1 | 2/2002 | Roth |
| 5,976,178 A | 11/1999 | Goldsteen et al. | 6,346,112 B2 | 2/2002 | Adams |
| 5,984,917 A | 11/1999 | Fleischman et al. | 6,350,269 B1 | 2/2002 | Shipp et al. |
| 5,984,959 A | 11/1999 | Robertson et al. | 6,352,543 B1 | 3/2002 | Cole |
| 5,989,242 A | 11/1999 | Saadat et al. | 6,358,258 B1 | 3/2002 | Arcia et al. |
| 5,989,268 A | 11/1999 | Pugsley, Jr. et al. | 6,361,559 B1 | 3/2002 | Houser et al. |
| 5,989,276 A | 11/1999 | Houser et al. | 6,368,348 B1 | 4/2002 | Gabbay |
| 5,989,278 A | 11/1999 | Mueller | 6,371,964 B1 | 4/2002 | Vargas et al. |
| 5,993,467 A | 11/1999 | Yoon | 6,387,105 B1 | 5/2002 | Gifford, III et al. |
| 5,993,468 A | 11/1999 | Rygaard | 6,391,038 B2 | 5/2002 | Vargas et al. |

| Patent No. | Date | Inventor |
|---|---|---|
| 6,402,764 B1 | 6/2002 | Hendricksen et al. |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 | 12/2002 | Ferrera et al. |
| 6,497,710 B2 | 12/2002 | Yencho et al. |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,288 B2 | 3/2003 | Vargas et al. |
| 6,547,799 B2 | 4/2003 | Hess et al. |
| 6,551,332 B1 | 4/2003 | Nguyen et al. |
| 6,562,053 B2 | 5/2003 | Schulze et al. |
| 6,575,985 B2 | 6/2003 | Knight et al. |
| 6,589,255 B2 | 7/2003 | Schulze et al. |
| 6,607,541 B1 | 8/2003 | Gardiner et al. |
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth |
| 6,918,917 B1 | 7/2005 | Nguyen |
| 6,921,407 B2 | 7/2005 | Nguyen et al. |
| 6,926,730 B1 | 8/2005 | Nguyen |
| 6,945,980 B2 | 9/2005 | Nguyen |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,182,769 B2 | 2/2007 | Ainsworth |
| 7,220,268 B2 | 5/2007 | Blatter |
| 2001/0018592 A1 | 8/2001 | Schaller |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0191481 A1 | 10/2003 | Nguyen |
| 2003/0195531 A1 | 10/2003 | Gardiner et al. |
| 2003/0199974 A1 | 10/2003 | Lee |
| 2004/0050393 A1 | 3/2004 | Golden |
| 2004/0068276 A1 | 4/2004 | Golden |
| 2004/0102797 A1 | 5/2004 | Golden et al. |
| 2004/0111099 A1 | 6/2004 | Nguyen |
| 2004/0138685 A1 | 7/2004 | Clague et al. |
| 2004/0176663 A1 | 9/2004 | Edoga |
| 2004/0193259 A1 | 9/2004 | Gabbay |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller |
| 2005/0075659 A1 | 4/2005 | Realyvasquez |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 | 5/2005 | Realyvasquez |
| 2005/0131429 A1 | 6/2005 | Ho |
| 2005/0267572 A1 | 12/2005 | Schoon et al. |
| 2006/0004389 A1 | 1/2006 | Nguyen et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |

FOREIGN PATENT DOCUMENTS

| | | |
|---|---|---|
| DE | 0377052 | 6/1923 |
| DE | 2703529 | 1/1977 |
| DE | 3203410 | 5/1981 |
| DE | 3227984 | 2/1984 |
| DE | 3504202 | 8/1985 |
| DE | 4133800 | 10/1991 |
| DE | 4402058 | 4/1995 |
| DE | 19547617 | 9/1997 |
| DE | 19732234 | 1/1999 |
| EP | 0072232 | 2/1983 |
| EP | 0122046 | 3/1983 |
| EP | 0129441 | 12/1984 |
| EP | 0130037 | 1/1985 |
| EP | 0140557 | 5/1985 |
| EP | 0121362 | 9/1987 |
| EP | 0409569 | 1/1991 |
| EP | 0432692 | 6/1991 |
| EP | 0478949 | 8/1991 |
| EP | 0494636 | 7/1992 |
| EP | 0537955 | 4/1993 |
| EP | 0559429 | 9/1993 |
| EP | 0598529 | 5/1994 |
| EP | 0326426 | 12/1994 |
| EP | 0419597 | 12/1994 |

| | | |
|---|---|---|
| EP | 0632999 | 1/1995 |
| EP | 0641546 | 3/1995 |
| EP | 0656191 | 6/1995 |
| EP | 0687446 | 12/1995 |
| EP | 0705568 | 4/1996 |
| EP | 0711532 | 5/1996 |
| EP | 0705569 | 10/1996 |
| EP | 0734697 | 10/1996 |
| EP | 0778005 | 6/1997 |
| EP | 0815795 | 1/1998 |
| GB | 2223410 | 4/1990 |
| JP | 07308322 | 11/1995 |
| JP | 08336544 | 12/1996 |
| JP | 10337291 | 12/1998 |
| RU | 2110222 | 5/1998 |
| SU | 577022 | 10/1977 |
| SU | 1186199 | 10/1985 |
| SU | 1456109 | 2/1989 |
| SU | 1560133 | 4/1990 |
| WO | 90/06725 | 6/1990 |
| WO | 90/09149 | 8/1990 |
| WO | 90/14795 | 12/1990 |
| WO | 91/07916 | 6/1991 |
| WO | 91/08708 | 6/1991 |
| WO | 91/17712 | 11/1991 |
| WO | 92/05828 | 4/1992 |
| WO | 92/12676 | 8/1992 |
| WO | 92/22041 | 12/1992 |
| WO | 93/01750 | 2/1993 |
| WO | 94/15535 | 7/1994 |
| WO | 94/15537 | 7/1994 |
| WO | 96/00035 | 1/1996 |
| WO | 96/06565 | 3/1996 |
| WO | 96/38090 | 12/1996 |
| WO | 97/12555 | 4/1997 |
| WO | 97/16122 | 5/1997 |
| WO | 97/27898 | 8/1997 |
| WO | 97/28744 | 8/1997 |
| WO | 97/31575 | 9/1997 |
| WO | 97/32526 | 9/1997 |
| WO | 97/40754 | 11/1997 |
| WO | 97/42881 | 11/1997 |
| WO | 98/19636 | 5/1998 |
| WO | 98/30153 | 7/1998 |
| WO | 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62408 | 12/1999 |
| WO | 99/62415 | 12/1999 |
| WO | 99/63910 | 12/1999 |
| WO | 99/65409 | 12/1999 |
| WO | WO 99/62406 | 12/1999 |
| WO | WO 99/62409 | 12/1999 |
| WO | WO 00/03759 | 1/2000 |
| WO | 00/15144 | 3/2000 |
| WO | 00/59380 | 10/2000 |
| WO | 00/60995 | 10/2000 |
| WO | WO 00/64381 | 11/2000 |
| WO | 00/74603 | 12/2000 |
| WO | 01/19292 | 3/2001 |
| WO | WO 01/26557 | 4/2001 |
| WO | WO 01/26586 | 4/2001 |
| WO | WO 01/28432 | 4/2001 |
| WO | 01/54618 | 8/2001 |
| WO | 01/74254 | 10/2001 |
| WO | 02/13701 | 2/2002 |
| WO | 02/13702 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/058170 | 6/2005 |

OTHER PUBLICATIONS

Emery, et al., Suture Techniques for MIDCAB Surgery, Techniques for Minimally Invasive Direct Coronary Artery Bypass (MIDCAB) Surgery, R.W. Emery ed., Hanley & Belfus, Inc.: Philadelphia, PA, Chapter 12, 1997, pp. 87-91.
Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Rabago, et al., The New De Vega Technique in Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty for Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462.
International Search Report PCT/US98/00795.
International Search Report PCT/US98/14211.
International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report on Patentability PCT/US2004/023728.
US 6,503,260, 01/2003, Schaller et al. (withdrawn)

\* cited by examiner

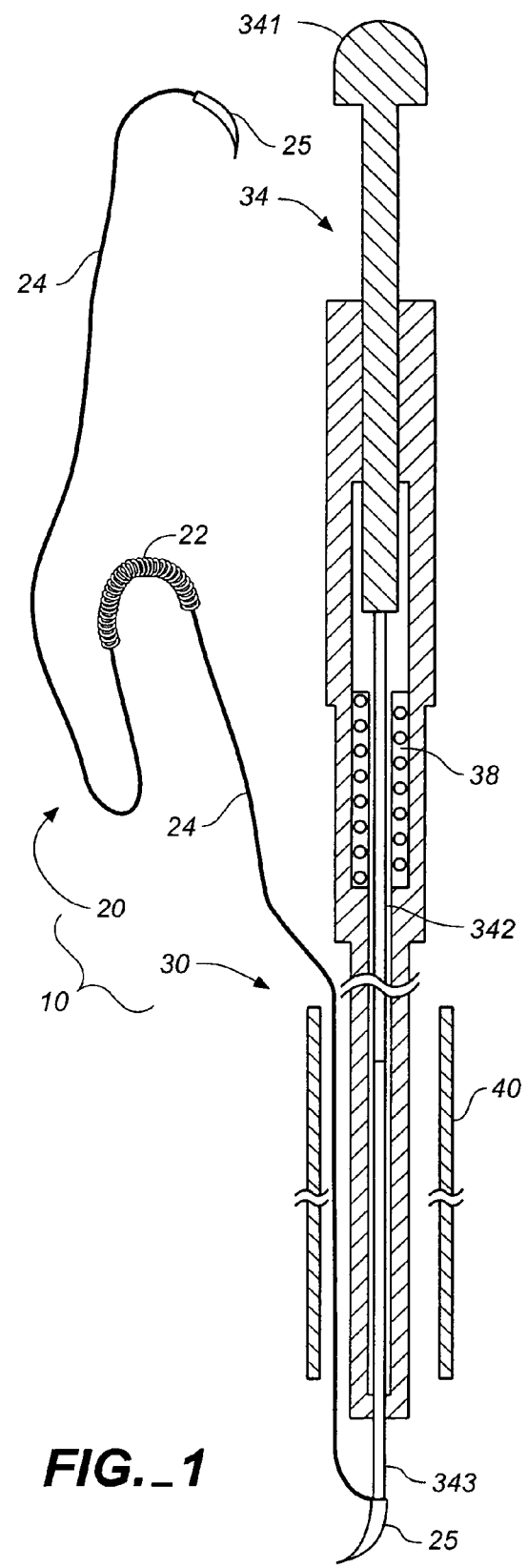
FIG._1

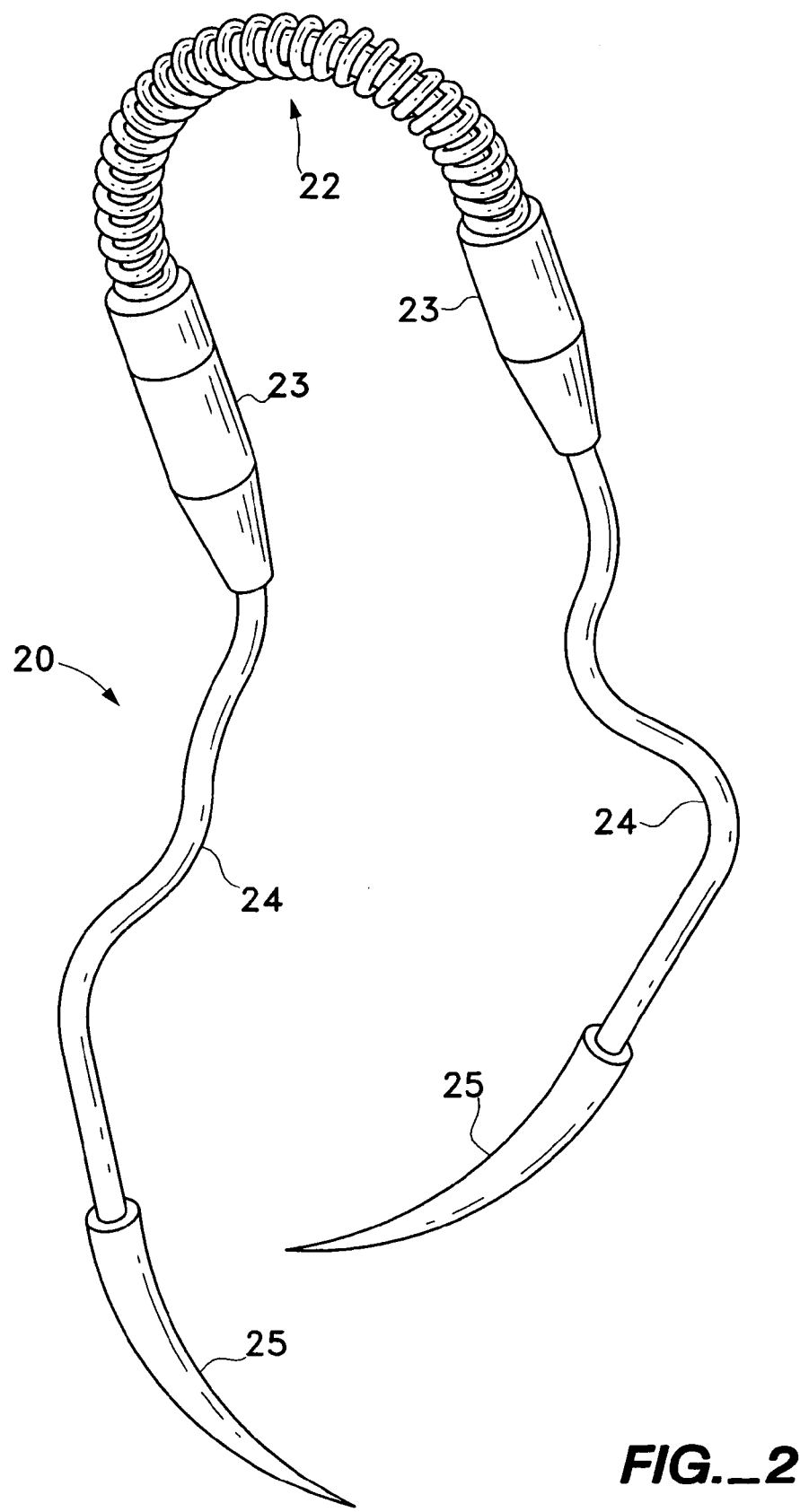
FIG._2

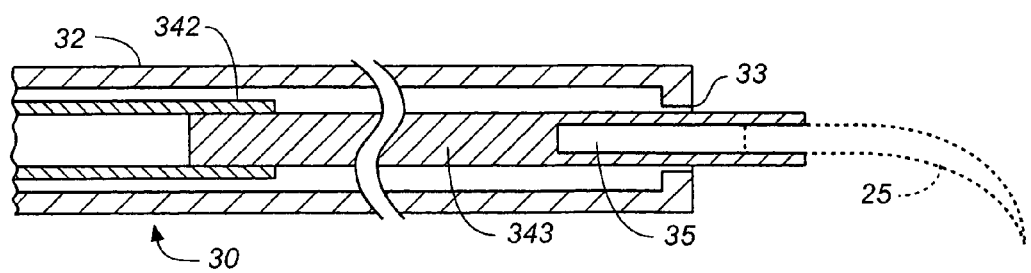
FIG._3
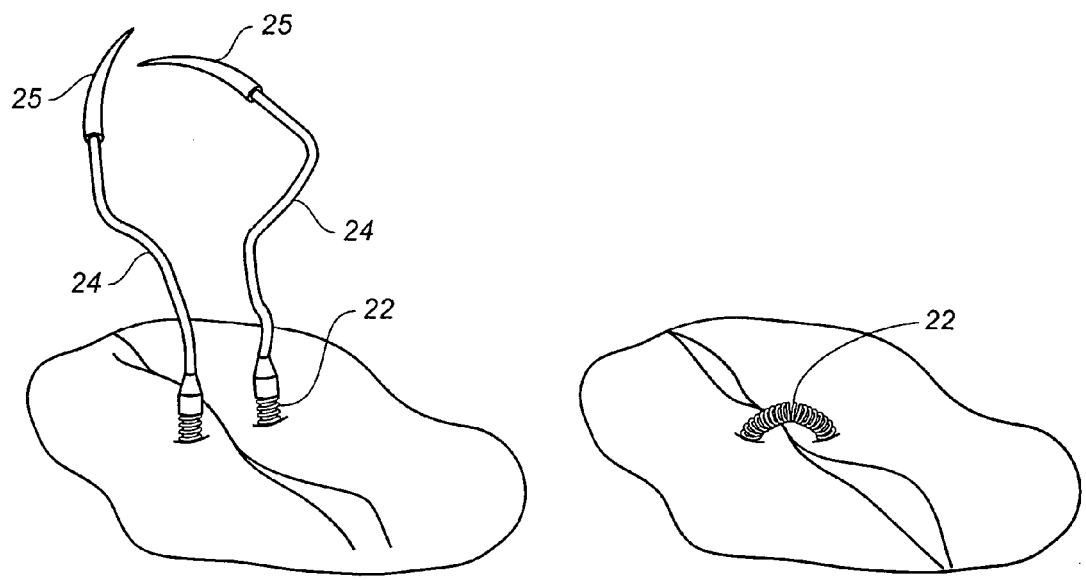
FIG._4A  FIG._4B

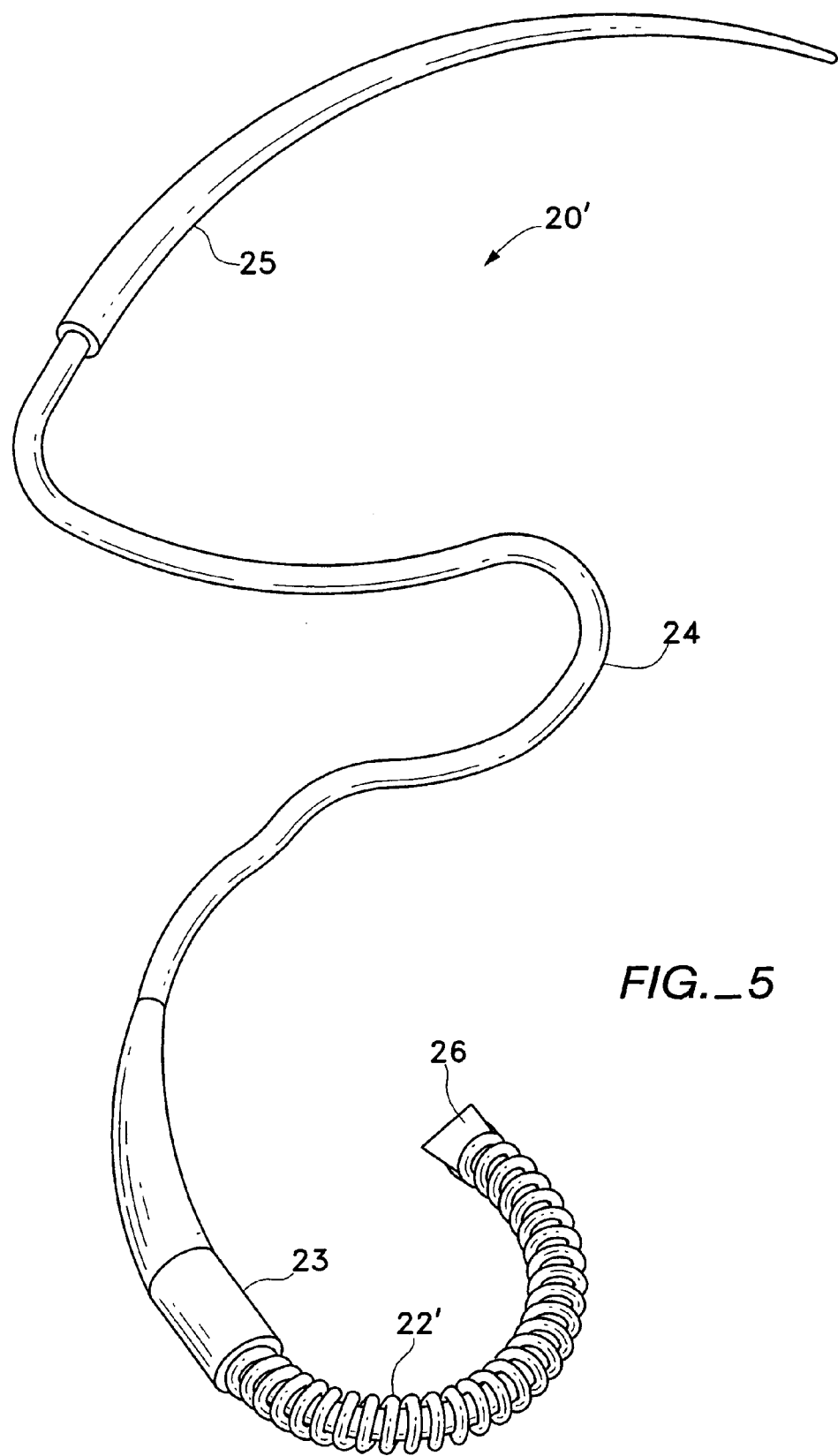
FIG._5

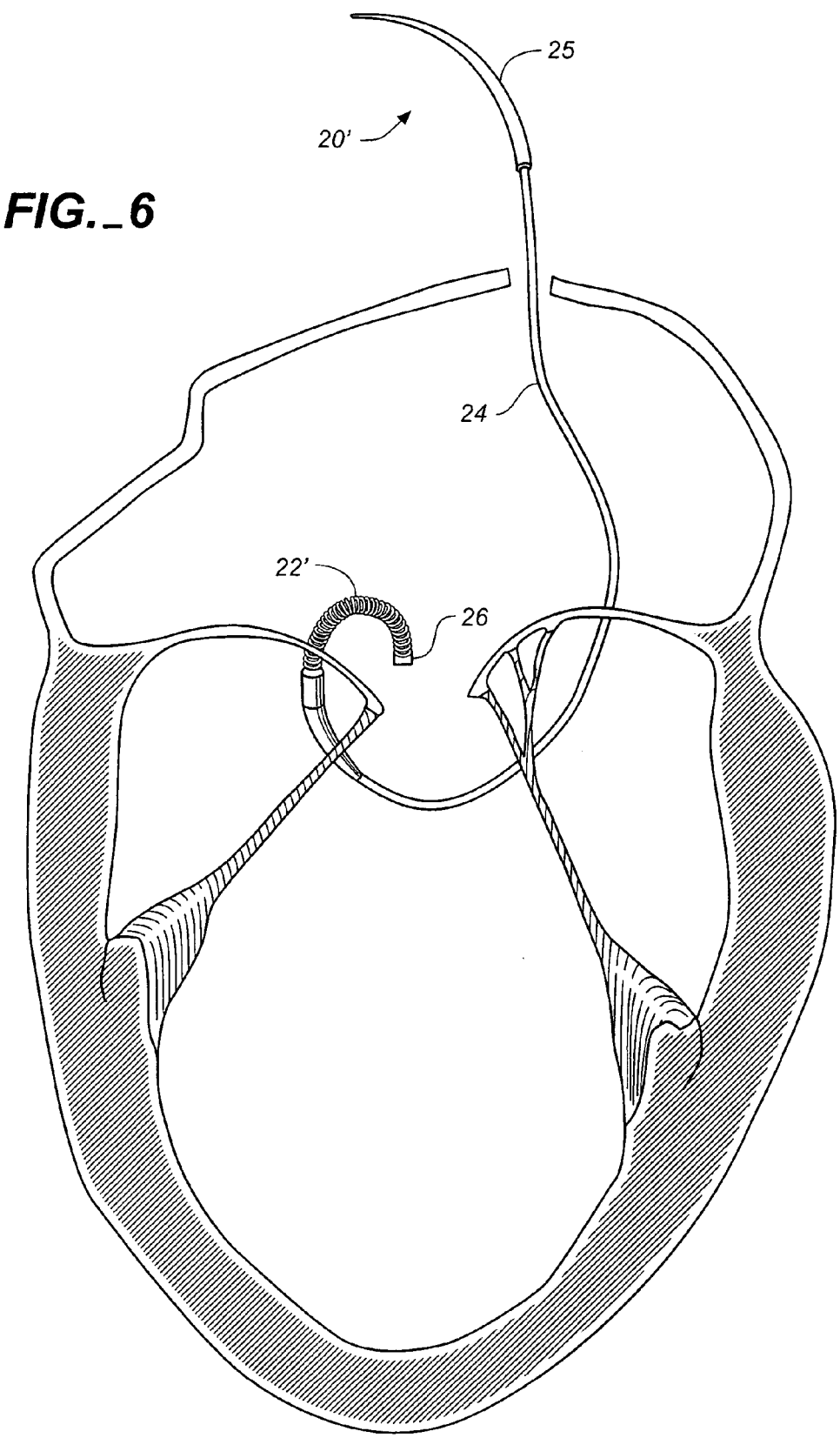
*FIG._6*

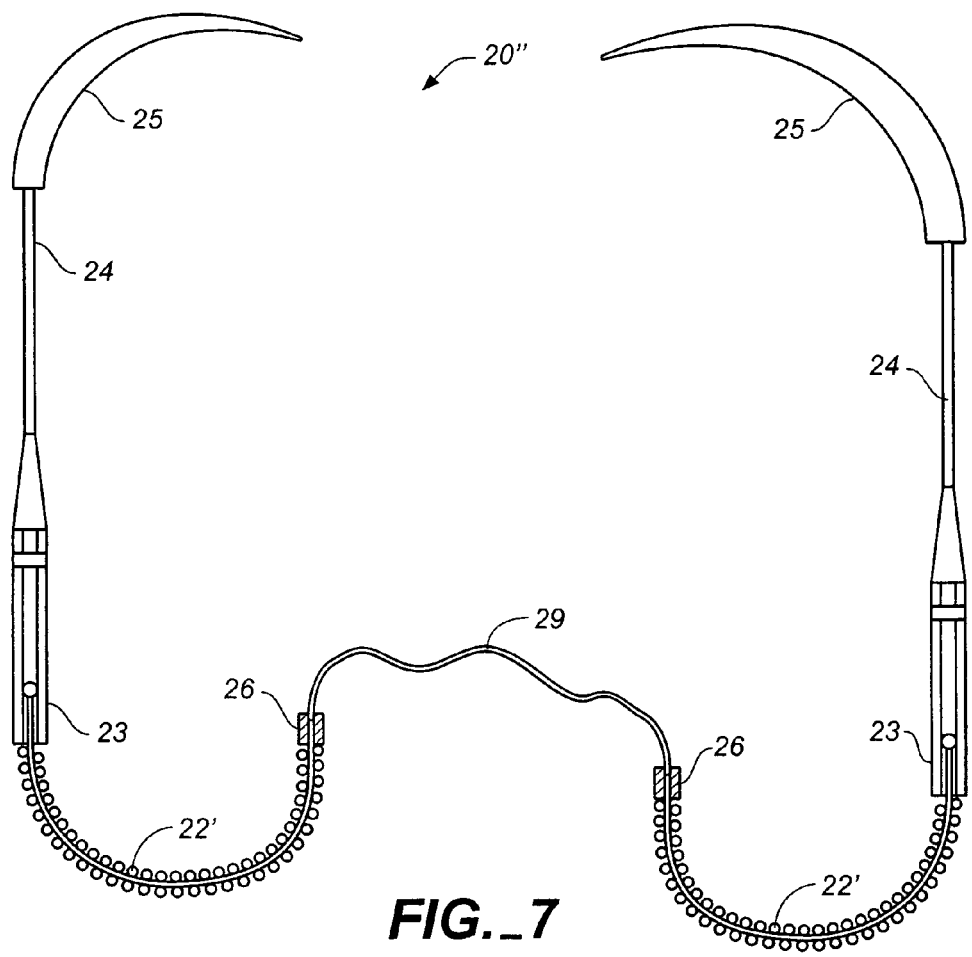
FIG._7
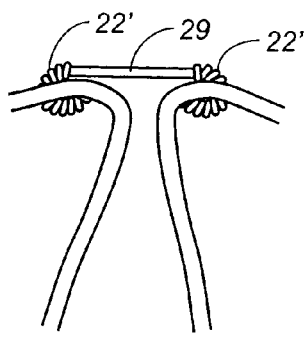
FIG._8A
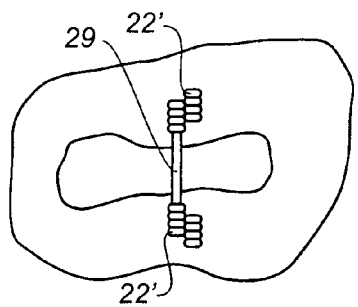
FIG._8B
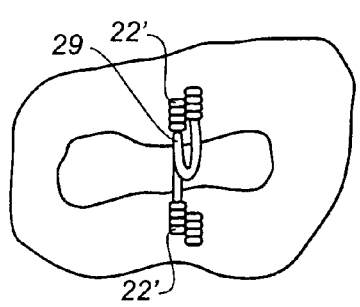
FIG._8C

MINIMALLY INVASIVE VALVE REPAIR PROCEDURE AND APPARATUS

CROSS REFERENCE TO RELATED APPLICATION(S)

This application is a continuation of U.S. patent application Ser. No. 09/686,004, entitled Minimally Invasive Valve Repair Procedure and Apparatus and filed on Oct. 10, 2000 now U.S. Pat. No. 6,926,730, which application is incorporated herein by reference in its entirety and to which we claim priority under 35 U.S.C. §120.

BACKGROUND OF THE INVENTION

This invention relates to methods and apparatus for minimally invasive valve repair and more particularly to minimally invasive methods and apparatus for reducing the valve orifice.

Valve repair is currently done in open surgical procedures as described, for example, by F. Maisano, et al. in their article entitled "The double-orifice technique as a standardized approach to treat mitral regurgitation due to severe myxomatous disease" which appeared in European Journal of Cardiothoracic Surgery, Vol. 17 (2000) 201-205. Cumbersome suture management, knot tying, pain and long recovery time are inherent to such open surgical procedures. It now goes without saying that minimally invasive surgery is the preferred procedure, having allowed surgeons to perform procedures with less pain and disability, than open surgical procedures. Tissue-connector apparatus and methods usable in such minimally invasive surgery procedures have recently been disclosed in U.S. patent application Ser. Nos. 09/089,884 and 09/090,305 both filed Jun. 3, 1998 and Ser. Nos. 09/259,705 and 09/260,623 both filed Mar. 1, 2000.

It is therefore a general object of this invention to provide improved minimally invasive methods and apparatus for coaptation of leaflets in the case of regurgitation to reduce the annular orifice.

It is a more specific object of this invention to provide such improved minimally invasive methods and apparatus using a tissue-connector apparatus disclosed in aforementioned U.S. patent applications.

SUMMARY OF THE INVENTION

Methods and apparatus embodying this invention with which the above and other objects can be accomplished are characterized as using a clip of a self-closing type as a tissue connector to capture leaflets and secure them together. Such a clip is typically U-shaped, having two end points, when it is constrained to be in an open configuration but is made of a wire of a shape memory material such that it tends to coil up to assume its natural closed configuration. Thus, if such a clip is placed between a pair of valve leaflets to be repaired, having each of its end points penetrating and completely passing through a different one of the leaflets while being constrained to be in its open configuration, and if the constraint which has been keeping the clip in its open configuration is then removed, it naturally tends to coil up, although it will not come to assume its natural closed configuration because it is hooked to the leaflets, tending nevertheless to reduce the distance of separation between its two end points. This has the effect of holding the leaflets together.

Such a clip may be deployed in the form of a clip assembly, having at least one of the end points of the clip connected to a tissue-piecing needle through a flexible member such as a suture and a release mechanism by which the clip can be easily released. The needle is attached to the front end of a needle-holder and passed through a cannula inserted through an incision towards the valve leaflets to be repaired. The needle-holder, according to a preferred embodiment of the invention, is formed with an outer tube and an inner member which is slidable inside the outer tube and is designed such that as the inner member is pushed forward against the biasing force of a spring contained in the outer tube, a slit which is provided at the front end becomes wider for accepting the needle therein but as the inner member is allowed to move to a backward position, the slit becomes narrower and grips the needle tightly.

BRIEF DESCRIPTION OF THE DRAWINGS

The accompanying drawings, which are incorporated in and form a part of this specification, illustrate embodiments of the invention and, together with the description, serve to explain the principles of the invention. In the drawings:

FIG. 1 is a schematic view of a tissue-connector apparatus embodying this invention when it is about to be used, its double-arm clip assembly being shown as a diagonal view and its needle holder being shown as a sectional side view;

FIG. 2 is an enlarged external view of the double-arm clip assembly of FIG. 1;

FIG. 3 is an enlarged sectional view of a portion of the needle holder near its front end;

FIG. 4A is a schematic diagonal view of the clip assembly of FIGS. 1 and 2 being used in a valve repair procedure embodying this invention, and FIG. 4B is another schematic diagonal view of the clip of FIG. 4A after it has been released;

FIG. 5 is an external view of a single-arm clip assembly which may be used in a method of minimally invasive valve repair embodying this invention;

FIG. 6 is a schematic sectional view for showing a method of valve repair embodying this invention by using the single-arm clip assembly of FIG. 5;

FIG. 7 is another clip assembly embodying this invention; and

FIG. 8A is a schematic sectional view of leaflets repaired by a clip assembly of FIG. 7, FIG. 8B is a top view of the leaflets of FIG. 8A, and FIG. 8C is a top view of leaflets repaired in an alternative manner.

Throughout herein like components are indicated by the same numerals even where they are components of different assemblies and may not necessarily described repetitiously.

The schematic drawings are intended to be indeed schematic and only to show the basic concepts of the invention, not necessarily representing realistic views, for example, with realistic relative sizes of body components and apparatus components.

DETAILED DESCRIPTION OF THE INVENTION

The invention is described next by way of examples. FIG. 1 shows schematically a tissue-connector apparatus 10 embodying this invention for a minimally invasive procedure. Described briefly, the apparatus 10 consists of a clip assembly 20 and a needle holder 30, which will be described next sequentially in detail.

The clip assembly 20 according to this embodiment may be referred to as the double-arm clip assembly, characterized as having a clip 22 of a self-closing type with two end points each connected through a flexible member 24 such as a suture to a tissue penetrating needle 25 (as disclosed, for example, in aforementioned U.S. patent application Ser. Nos. 09/259,705 and 09/260,623 both filed Mar. 1, 2000, both of which are herein incorporated by reference). Each of the needles 25 has a tissue-piercing sharp point and is connected to a corresponding one of the flexible members 24. As shown more clearly in FIG. 2, the two end points of the clip 22 are each provided with and directly connected to a release mechanism 23 such that it can be released easily from the flexible members 24 and from being constrained to remain in its generally U-shaped open configuration.

The clip 22, or a surgical fastener, of the so-called self-closing type may be one disclosed in aforementioned U.S. patent application Ser. Nos. 09/089,884 and 09/090,305 both filed Jun. 3, 1998 (herein also incorporated by reference), as well as in aforementioned U.S. patent application Ser. Nos. 09/259,705 and 09/260,623, characterized as having two end points, being generally U-shaped when in an open configuration (as shown in FIGS. 1 and 2), being naturally in a closed configuration (state or condition) and being elastic (or pseudoelastic, but herein broadly characterized as being "elastic") so as to tend to return to the closed configuration by reducing the separation distance between its end points when forced into an open configuration. As disclosed in aforementioned U.S. patent application Ser. Nos. 09/089,884 and 09/090,305, such a clip 22 may comprise a deformable wire made of a shape memory alloy such as a nickel titanium based alloy (nitinol). It is also known that the alloy may include additional elements, depending on the desired yield strength of the material or the temperature at which particular pseudoelastic or shape transformation characteristics occur. When the clip 22 is in its closed configuration (not shown) with no external restraining force thereupon, it may be in a completely closed loop with its end points in a side-by-side or overlapping orientation, the wire being looped by more than 360°. The diameter of the wire for the clip 22 and the diameter of the loop when it is in the closed configuration may be selected, depending on the application, and do not limit the scope of the invention.

The needle holder 30 consists essentially of a hollow outer tube 32, an inner member 34 and a spring 38, as shown in FIG. 1. The outer tube 32 is elongated, defining a longitudinal direction. The inner member 34 is also longitudinally elongated and is adapted to slide longitudinally inside the outer tube 32 and to releasably grab the needles 25, one at a time. According to the embodiment shown in FIG. 1, the inner member 34 is comprised of a knob 341 at its proximal end, a conjunction tube 342 in the middle and a needle-holding tube 343 in front. The conjunction tube 342 and the needle holding tube 343 are laser-welded together. A threaded adapter is laser-welded to the proximal end of the conjunction tube 342 for allowing the knob 341 to be screwed thereonto after the spring 38 is inserted inside the outer tube 32 such that, once the needle holder 30 is thus assembled, the knob 341, the conjunction tube 342 and the needle-holding tube 343 will move together as a single unit. The front end of the needle-holding tube 343 is provided with a longitudinally elongated slit 35 for holding the needle 25, and the outer tube 32 has a front opening 33, as shown more clearly in FIG. 3. The needle-holding tube 343 with the slit 35 and the front opening 33 of the outer tube 32 are so designed that the slit 35 will open and become sufficiently wide in front as the inner member 34 is pushed forward through the outer tube 32 for accepting a needle 25 (shown by broken lines in FIG. 3) therein and that the opening of the slit 35 tends to become smaller as the inner member 34 is moved backwards through the outer tube 32 so as to retract the needle-holding tube 343 through the front opening 33 of the outer tube 32, causing the needle-holding tube 343 to securely grab the needle 25 once accepted. The spring 38 is disposed inside the outer tube 32 so as to provide a backward biasing force on the inner member 34. In other words, the inner member 34 is normally in a backward position inside the outer tube 32 under the influence of the backward biasing force of the spring 38 thereon. As the user pushes the inner member 34 forward by operating the knob 341 against aforementioned backward biasing force of the spring, the front part of the needle-holding tube 343 protrudes further outward from the front opening 33 of the outer tube 32 and the slit 35 opens wider, its front opening becoming wide enough to accept the back part of a needle (away from its tissue-piercing sharp point). If the user then releases the force being applied to the knob 341 after the back part of the needle 25 has been accepted inside the slit 35, the backward biasing force by the spring pushes the inner member 34 backward, reducing the length of the needle-holding tube 343 outside the front opening 33 of the outer tube 32. This has the effect of reducing the opening of the slit 35 and hence of having the needle 25 firmly gripped by the needle holder 30. In summary, the user pushes the knob 341 forward to accept the needle 25 and releases the force on the knob 341 to firmly grab it. When a needle is already being held by the needle holder 30, the user has only to push the knob 341 to release it.

A valve repair procedure embodying this invention, such as for reducing the valve orifice by using the apparatus described above, will be described next.

To access a mitral valve, a small incision is made on the appendage of the left atrium. One of the needles 25 of the clip assembly 20 is grabbed by the needle holder 30, as shown in FIG. 1, by pushing the knob 341 forward to accept the needle 25 and then releasing it to firmly attach the needle 25 to the needle holder 30, as described above. A cannula is inserted into the incision. FIG. 1 shows the cannula schematically at 40 but the patient's body part are omitted from FIG. 1. With an aid of an ultrasound machine (not shown), the needle holder 30 is passed through the cannula 40 towards the leaflets, and the needle 25 held by the needle holder 30 is caused to penetrate and be completely pulled through one of the leaflets. Thereafter, the knob 341 is pushed forward to release the needle 25. The knob 341 is pushed forward again to grab the same needle 25 from the other side of the leaflet to secure the needle 25 on the leaflet. Thereafter, the needle 25 is released, the needle holder 30 is pulled out of the cannula 40 and the other of the needles 25 of the double-arm clip assembly 20 is similarly grabbed by its needle holder 30. The same procedure as described above is repeated to cause the second needle 25 of the clip assembly 20 to penetrate and be completely pulled through and be secured to the other of the leaflets. The needles 25 are pulled, together with the flexible members 24 attached thereto, until the clip 22 comes to span the leaflets, as shown in FIG. 4A. Thereafter, the release mechanisms 23 are squeezed by an instrument such as the needle holder 30 itself to release the clip 22 from the flexible members 24. Free of constraints, the clip 22 now tends to return to its natural closed configuration, reducing the distance separating its two end points. This has the effect of tightly bringing the leaflets together, as shown in FIG. 4B, thereby reducing the valve orifice.

The invention was described above by way of only one example but this example is not intended to limit the scope of the invention. Many modifications and variations are possible within the scope of the invention. For example, although the use of a clip assembly having two needles each connected to a corresponding one of the two end points of a generally U-shaped clip was disclosed, use may be made under certain circumstances of a simpler single-arm clip assembly 20' shown in FIG. 5 and described, for example, in aforementioned U.S. patent application Ser. Nos. 09/089,884 and 09/090,305, having only one needle 25 attached through a flexible member 24 and a release mechanism 23 to one of the two end points of a clip 22'. Such a single-arm clip assembly 20' may be used similarly, as described above in connection with the double-arm clip assembly 20 shown in FIGS. 1 and 2, except that the clip 22' is provided with a stopper 26 at the other of its two end points not connected to the flexible member 24 for keeping the clip 22' in its generally U-shaped open configuration. After the needle 25 is caused to penetrate both leaflets, as shown in FIG. 6, the clip 22' can be caused to pull the two leaflets together as the flexible member 24 is pulled, the stopper 26 serving to locate the clip 22' across the leaflets.

FIG. 7 shows still another clip assembly 20" embodying this invention, indicating like components by the same numerals as used in FIGS. 2 and 5. This clip assembly 20" is characterized as having not only two tissue penetrating needles 25 each connected to a flexible member 24 but also two self-closing clips 22' as shown in and explained with reference to FIG. 5, each having a stopper 26 at one end point for keeping the clip 22' in a generally U-shaped open configuration and the other end point being connected to a corresponding one of the flexible members 24 through a release mechanism 23 for separating the clip 22' from the flexible member 24 and thereby releasing the clip 22' from remaining in its open configuration. These two clips 22' are connected through their stoppers 26 by another flexible member 29 which may be a suture or a metal wire.

A clip assembly 22' thus structured may be used in a valve repair procedure, for example, by penetrating a leaflet tissue with one of the needles 25, causing it to come up and out at another position in a manner of ordinary stitching, pulling the associated flexible member 24 until the clip 22' connected thereto penetrates the leaflet tissue partially such that the end point of this clip 22' on the side of the release mechanism 23 penetrates the tissue and reappears on the surface while the other end point on the side of the stopped 26 does not penetrate the tissue, and doing the same with the other needle 25 on the leaflet on the opposite side of the valve opening. After the release mechanisms 23 on both clips 22' are pressed, as described above, to release the clips 22' from the needles 25, each clip 22' tends to coil up, getting firmly attached to the respective leaflet, the flexible member 29 therebetween holding the leaflets together, as shown in FIGS. 8A and 8B. In other words, it is the flexible member 29 between the two clips 22' that holds the leaflets together. As an alternative procedure, the needles 25 may be operated such that the connecting flexible member 29 makes a loop between the leaflets, as shown in FIG. 8C.

Although the clips 22 and 22', when constrained to an open configuration before they are released from the flexible member 24, are described as being generally U-shaped, this description is intended to be interpreted broadly. As should be clear from the intended function of the clips 22 and 22', their open configuration may look more like a C or a J than a U. The release mechanisms 23, described above as serving to release the connection between the clip 22 or 22' and the flexible members 24 and to release the clip 22 or 22' from its forced open configuration, may be structured as disclosed in aforementioned U.S. patent application Ser. No. 09/260,623 but their structure is not intended to limit the scope of the invention.

In summary, the disclosure is intended to be interpreted broadly. Although the invention has been described as being addressed to a method and an apparatus for valve repair, a person skilled in the art will immediately realize that the method and apparatus of this invention as described above can be used for holding two tissue parts close together, not being limited to valve leaflets. The scope of this invention, therefore, is to be understood as including methods of and apparatus for holding two tissue parts close together.

What is claimed is:

1. A clip assembly comprising:
   two clips each having two end points, a proximal end point and a distal end point, the proximal end point and the distal end point being separated from each other when said clip is held in an open configuration and tending to return to a naturally closed configuration wherein the distance between said proximal end point and said distal end point is reduced;
   two tissue penetrating needles each releasably connected to one of said two end points of a corresponding one of said two clips through a flexible member; and
   a flexible connector connecting the other end points of said two clips together.

2. The clip assembly of claim 1 wherein said clips comprise a wire made of a shape memory material.

3. The clip assembly of claim 1 further comprising releasing means for normally keeping the two clips in the open configuration and releasing each of the two clips to become separated from the associated flexible member to thereby allow the clips to begin returning to the closed configuration.

4. The clip assembly of claim 1 wherein each of said clips further comprise a stopper connected to one of said two end points of said clip.

5. The clip assembly of claim 1 wherein the flexible connector comprises a suture.

6. The clip assembly of claim 1 wherein the flexible connector comprises a metal wire.

7. A clip assembly comprising:
   two clips each having two end points which are separated from each other when said clips are in an open configuration and tending to return to a naturally closed configuration by reducing distance between said end points when the clip is in said open configuration;
   two tissue penetrating needles each connected to one of said two end points of a corresponding one of said two clips through a flexible member; and
   a flexible connector connecting the other end points of said two clips together; and
   releasing means for normally keeping said two clips in said open configuration and releasing each of said two clips to become separated from the associated flexible member to thereby allow said clips to begin returning to said closed configuration.

8. The clip assembly of claim 7 wherein the clips comprise a wire made of a shape memory material.

9. The clip assembly of claim 7 wherein each of said clips further comprise a stopper connected to one of said two end points of said clip.

10. The clip assembly of claim 7 wherein the flexible connector comprises a suture.

11. The clip assembly of claim 7 wherein the flexible connector comprises a metal wire.

12. A minimally invasive method of holding two tissue parts together, said method comprising the steps of:
   providing a clip assembly which comprises two clips each having two end points which are separated from each other when said clips are in an open configuration and tending to return to a naturally closed configuration by reducing distance between said end points when the clip is in said open configuration, two tissue penetrating needles each releasably connected to one of said two end points of a corresponding one of said two clips through a flexible member, and a flexible connector connecting the other end points of said two clips together;

penetrating and completely pulling one of the needles through a tissue part and penetrating and completely pulling the other of the needles through an adjacent tissue part while said clips are each in said open configuration;

pulling the needles until each of said clips is hooked to a corresponding one of the tissue parts; and allowing said clips to start to return to said naturally closed configuration, whereby said two tissue parts are held together by said flexible connector stretched between said clips.

13. The method of claim 12 wherein said clips comprise a wire made of a shape memory material.

14. The method of claim 12 wherein said flexible connector forms a loop when stretched between said clips.

15. A minimally invasive method of holding two tissue parts together, said method comprising the steps of:

providing a clip assembly which comprises two clips each having two end points which are separated from each other when said clips are in an open configuration and tending to return to a naturally closed configuration by reducing distance between said end points when the clip is in said open configuration, two tissue penetrating needles each connected to one of said two end points of a corresponding one of said two clips through a flexible member, and a flexible connector connecting the other end points of said two clips together;

penetrating and completely pulling one of the needles through a tissue part and penetrating and completely pulling the other of the needles through an adjacent tissue part while said clips are each in said open configuration;

pulling the needles until each of said clips is hooked to a corresponding one of the tissue parts; and allowing said clips to start to return to said naturally closed configuration, whereby said two tissue parts are held together by said flexible connector stretched between said clips;

wherein said clip assembly further comprises releasing means for normally keeping said two clips in said open configuration and releasing each of said two clips to become separated from the associated flexible member to thereby allow said clips to begin returning to said closed configuration, and wherein said clips are allowed to start to return to said naturally closing configuration by separating said clips from said needles through said releasing means.

16. The method of claim 15 wherein said clips comprise a wire made of a shape memory material.

17. The method of claim 15 wherein said flexible connector forms a loop when stretched between said clips.

* * * * *